(12) United States Patent
Kamel et al.

(10) Patent No.: US 9,526,875 B2
(45) Date of Patent: Dec. 27, 2016

(54) ADJUSTABLE LENGTH DILATION BALLOON

(71) Applicant: Cook Medical Technologies LLC, Bloomington, IN (US)

(72) Inventors: Amro Kamel, Bloomington, IN (US); Brian Feng, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 233 days.

(21) Appl. No.: 14/528,793

(22) Filed: Oct. 30, 2014

(65) Prior Publication Data

US 2015/0119922 A1    Apr. 30, 2015

Related U.S. Application Data

(60) Provisional application No. 61/898,307, filed on Oct. 31, 2013.

(51) Int. Cl.
 *A61M 25/10* (2013.01)
 *A61M 25/00* (2006.01)
 *A61F 2/962* (2013.01)
 *A61F 2/95* (2013.01)

(52) U.S. Cl.
 CPC .............. *A61M 25/104* (2013.01); *A61F 2/95* (2013.01); *A61F 2/962* (2013.01); *A61M 2025/1068* (2013.01); *A61M 2025/1081* (2013.01)

(58) Field of Classification Search
 CPC ................... A61M 25/104; A61M 2025/1068; A61M 2025/1081; A61F 2/95; A61F 2/962

See application file for complete search history.

(56) References Cited

U.S. PATENT DOCUMENTS

| | | | |
|---|---|---|---|
| 4,564,014 A | 1/1986 | Fogarty et al. | |
| 4,820,270 A * | 4/1989 | Hardcastle | A61L 29/06 264/167 |
| 5,002,558 A | 3/1991 | Klein et al. | |
| 5,246,421 A | 9/1993 | Saab | |
| 5,514,093 A | 5/1996 | Ellis et al. | |
| 5,549,551 A | 8/1996 | Peacock, III et al. | |
| 5,647,857 A * | 7/1997 | Anderson | A61F 2/958 604/160 |
| 5,961,536 A | 10/1999 | Mickley et al. | |
| 6,066,155 A | 5/2000 | Amann et al. | |
| 6,238,410 B1 * | 5/2001 | Vrba | A61F 2/01 606/198 |
| 6,344,045 B1 * | 2/2002 | Lim | A61F 2/958 604/194 |
| 6,695,863 B1 | 2/2004 | Ramzipoor et al. | |
| 6,780,183 B2 | 8/2004 | Jimenez, Jr. et al. | |
| 6,884,257 B1 | 4/2005 | Cox | |
| 7,780,716 B2 | 8/2010 | Pappas et al. | |
| 7,799,065 B2 | 9/2010 | Pappas | |

(Continued)

FOREIGN PATENT DOCUMENTS

EP  0727194 A1  8/1996
WO  WO 2012/037507 A1  3/2012

*Primary Examiner* — Julian W Woo
(74) *Attorney, Agent, or Firm* — Brinks Gilson & Lione

(57) ABSTRACT

The present invention relates to an adjustable length dilatation balloon catheter that includes a balloon catheter, a sheath that is slidably disposed around the balloon catheter, and an inverting tethering system that permits the selective adjustment of the exposed balloon length.

12 Claims, 5 Drawing Sheets

(56) References Cited

U.S. PATENT DOCUMENTS

| | | |
|---|---|---|
| 2003/0100916 A1 | 5/2003 | Lee et al. |
| 2005/0055077 A1 | 3/2005 | Marco et al. |
| 2005/0182475 A1 | 8/2005 | Jen et al. |
| 2007/0191864 A1 | 8/2007 | Shumer |
| 2009/0105686 A1 | 4/2009 | Snow et al. |
| 2010/0228333 A1 | 9/2010 | Drasler et al. |
| 2014/0276530 A1* | 9/2014 | Gianotti ............ A61M 25/1002 604/500 |
| 2014/0276585 A1* | 9/2014 | Gianotti .......... A61M 25/10184 604/506 |

* cited by examiner

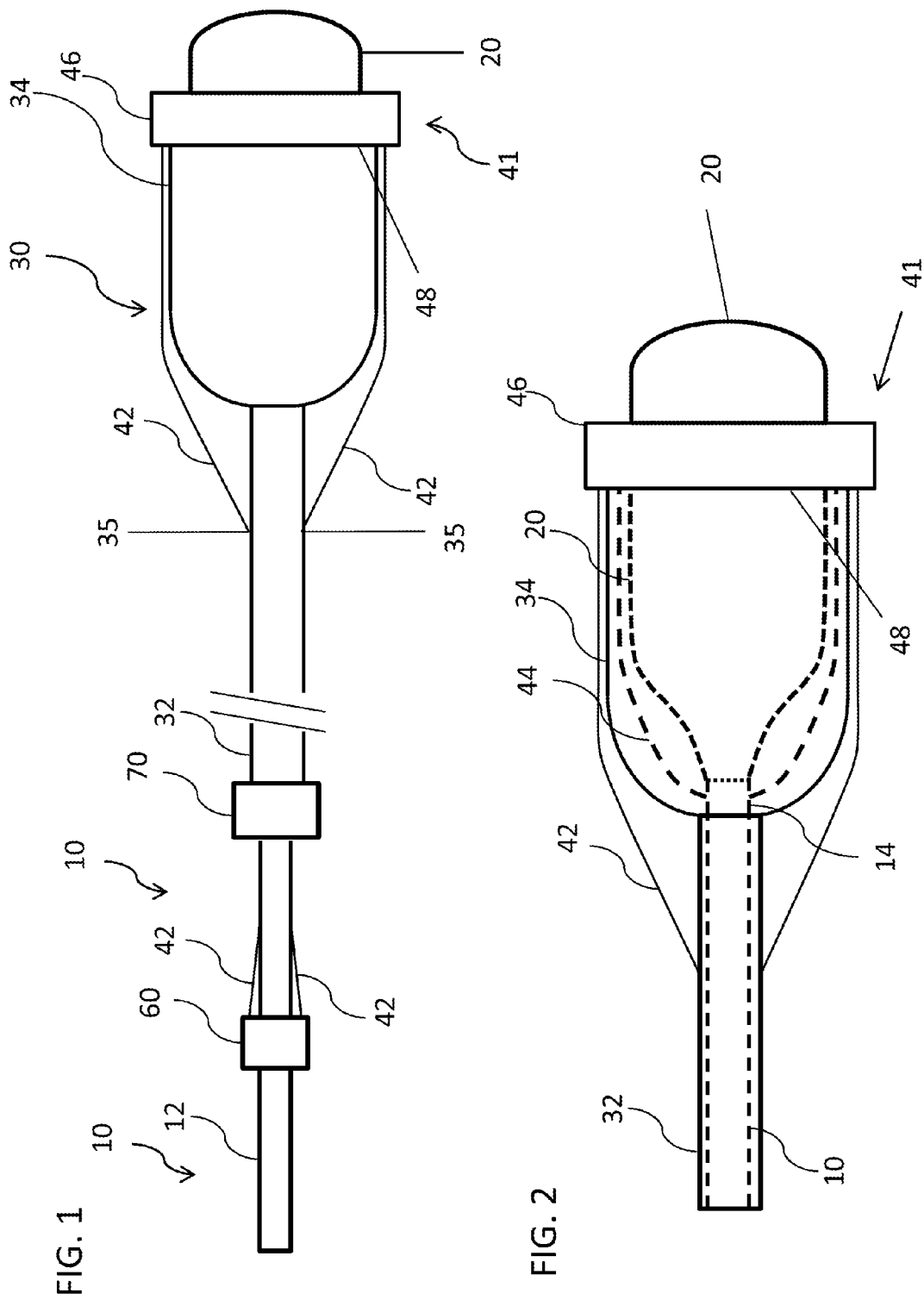

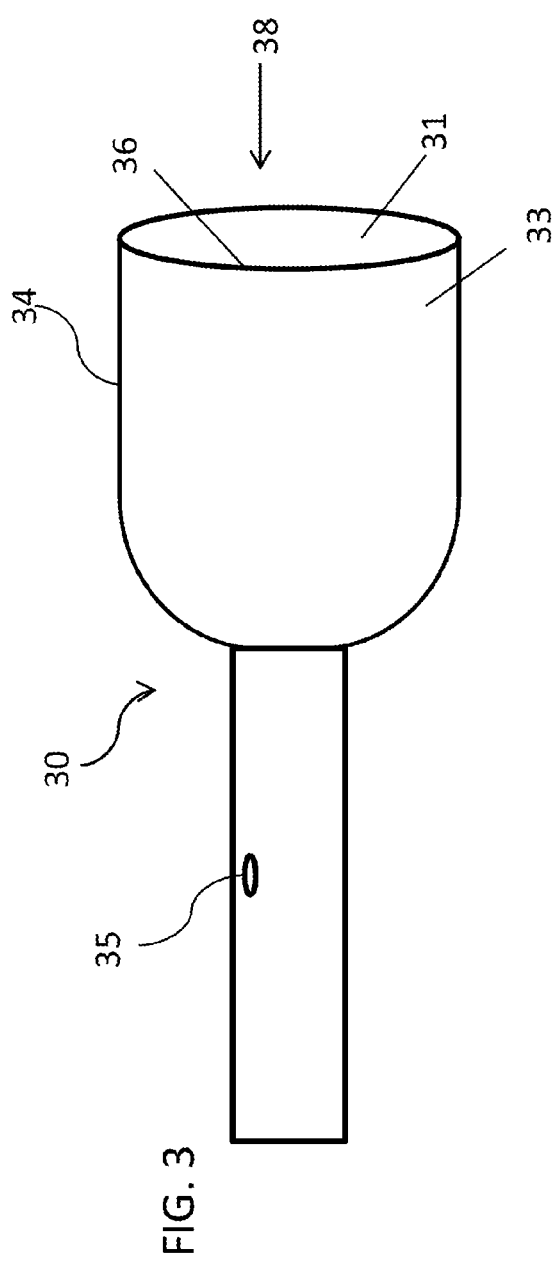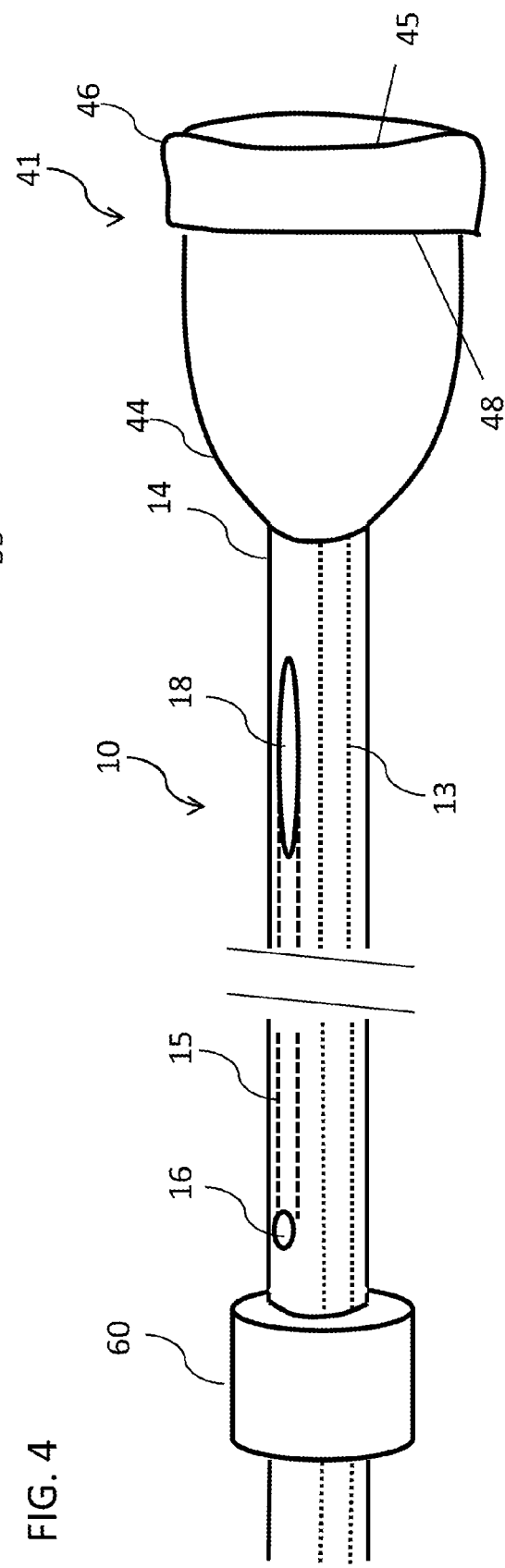

ADJUSTABLE LENGTH DILATION BALLOON

RELATED APPLICATIONS

The present patent document claims the benefit of the filing date under 35 U.S.C. §119(e) of Provisional U.S. Patent Application Ser. No. 61/898,307, filed Oct. 31, 2013, which is hereby incorporated by reference.

BACKGROUND OF THE INVENTION

1. Field of the Invention

The invention relates to balloon dilatation catheters and systems having an adjustable length balloon for use in percutaneous transluminal angioplasty (PTA).

2. Description of the Related Art

In certain clinical applications, there is a need to adjust the working length of a balloon in order to achieve ideal functionality. For example, when treating vascular stenoses (narrowing in blood vessel) using techniques such as PTA or venoplasty, the physician may encounter multiple stenoses of different lengths. The length of the balloon chosen for the procedure may not be appropriate for all stenoses. In these situations, using multiple balloons to dilate the stenoses may increase the complexity and cost of a procedure, as well as increase the inventory of different length balloons a hospital must have on hand. Thus, there is a need for catheter systems that permit the length of the exposed balloon to be controlled during a medical procedure.

SUMMARY OF THE INVENTION

The present invention relates to an adjustable length dilatation balloon catheter system having a balloon catheter, a sheath, and a tethering system for adjusting the exposed balloon length through the relative movement of the balloon catheter and the sheath.

In a first aspect, the invention provides a catheter having a proximal end, a distal end, an inflation lumen, and an external surface. Attached to the catheter distal end is a balloon in fluid communication with the inflation lumen. Slidably disposed around the catheter and balloon is a sheath, which has a proximal end, a distal end, and interior and exterior surfaces. The distal end of the sheath has an inner surface, an outer surface, and a lip that defines a sheath distal opening. Slidably disposed on the catheter external surface is a retraction cuff that is positioned proximal to the sheath proximal end and capable of being actuated in the proximal direction along a catheter longitudinal axis. In operative connection with the distal end of the catheter is an inverting sleeve, the operative connection being to a first end of the inverting sleeve. A portion of the sleeve variably extends along the inner surface of the sheath distal end, through the sheath distal opening, over the lip of the sheath, and along the outer surface of the sheath distal end. The retraction cuff is in operative connection with the inverting sleeve at a second end of the sleeve. The retraction cuff and the operative connection with the inverting sleeve are adapted to pull the sleeve into contact with the lip of the sheath thereby applying a first pulling force on the lip in the proximal direction. Simultaneous with the first pulling force, the lip of the sheath functions as a pivot point such that the sleeve applies a second pulling force on the catheter distal end in the distal direction.

In a second aspect, the invention provides a method of controllably deploying a length of balloon in a balloon catheter that is surrounded by a slidable sheath, where the sheath has a distal end and the distal end has an inner surface, an outer surface, and a lip that defines a distal opening. Simultaneous application of a first pulling force on the lip of the sheath in the proximal direction and a second pulling force on the distal end of the catheter in the distal direction effects a change in the relative positions of the sheath and the balloon, thereby exposing a length of the balloon through the sheath distal opening.

BRIEF DESCRIPTION OF THE DRAWINGS

FIG. 1 illustrates an exemplary embodiment of an adjustable length balloon dilatation catheter.

FIG. 2 illustrates a view of the overlay of the balloon, the inverting sleeve, and the sheath.

FIG. 3 illustrates an exemplary embodiment of a sheath.

FIG. 4 illustrates an exemplary embodiment of the catheter and inverting sleeve without the sheath.

DETAILED DESCRIPTION

Figures 5, 6:
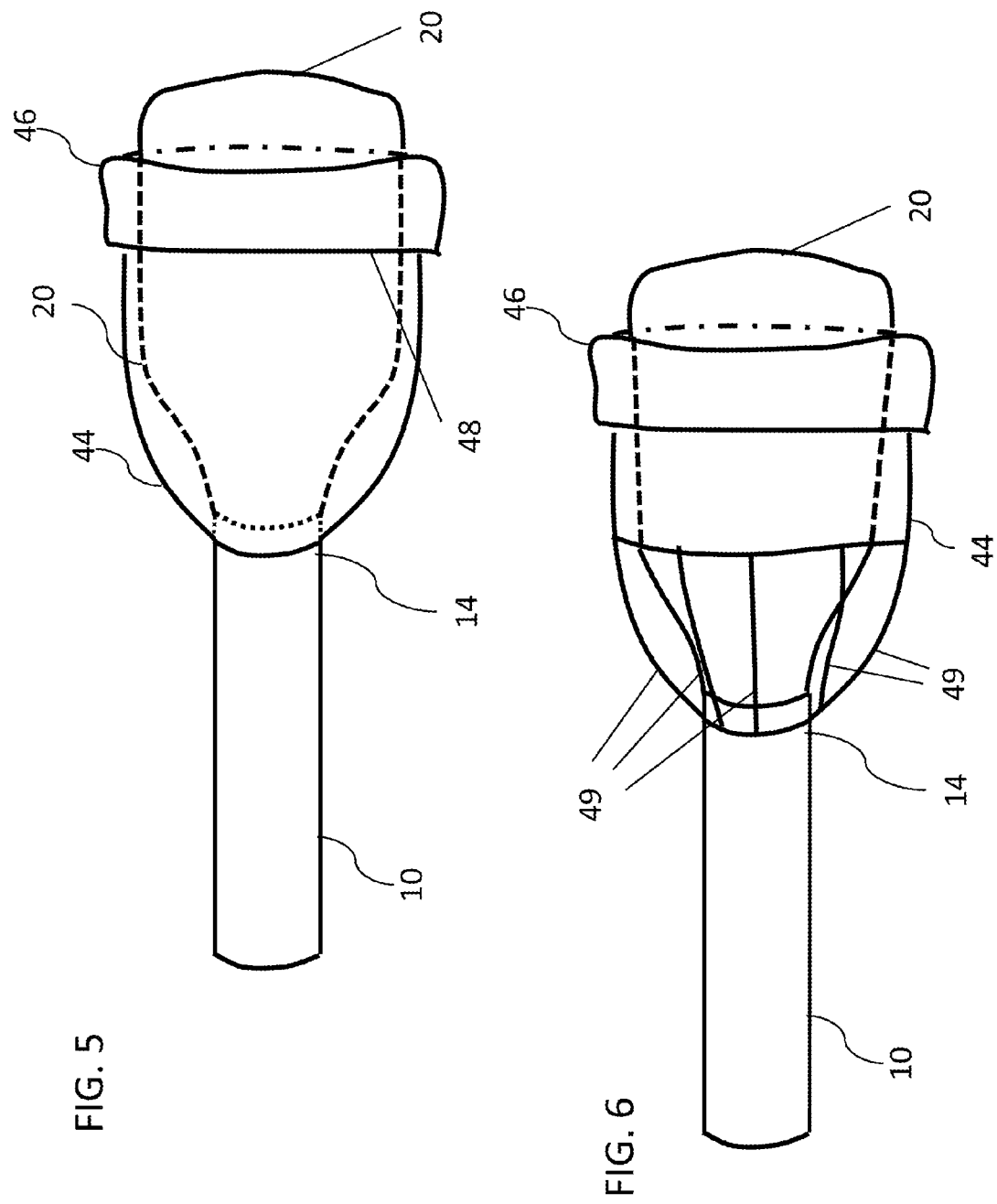
FIG. 5 illustrates a view of the overlay of the inverting sleeve and the balloon without the sheath.
FIG. 6 illustrates an alternate embodiment where the inverting sleeve is operatively connected to the catheter distal end by a second plurality of strands.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. For example, although the drawings and descriptions illustrate over-the-wire type designs, the invention is also suitable for use with rapid-peripheral exchange systems. It should also be understood that the drawings are not to scale and in certain instances details have been omitted, which are not necessary for an understanding of the embodiments, such as conventional details of fabrication and assembly.

An exemplary embodiment of an adjustable length balloon catheter system is illustrated in FIG. 1. A sheath 30 is slidably disposed around a catheter 10. The sheath 30 has a proximal end 32 and a distal end 34. On the proximal end is an optional grip 70 that may be used in some circumstances for advancing or retracting the sheath relative to the internal catheter. A balloon 20 is shown partially exposed through the distal opening of the sheath. Also shown in FIG. 1 are parts of an inverting tether system. The exemplary inverting tether system of FIG. 1 includes an inverting sleeve 41 that is operatively connected to a first plurality of strands 42 at the second end 48 of the sleeve 41. The strands extend in the proximal direction along the exterior of the sheath through apertures 35 in sheath 30, along the interior of the sheath, and through or alongside the catheter toward the proximal end of the catheter. The strands 42 are connected to a retraction cuff 60 that is slidably disposed around the catheter 10 at the proximal end 12 of the catheter in a location that is proximal to the sheath proximal end 32. Application of a pulling force on the retraction cuff 60 in the proximal direction translates the pulling force from the retraction cuff 60 through the strands 42 to the inverting sleeve 41. As will be explained in greater detail below, pulling on the inverting sleeve 41 in the proximal direction effects a change in the relative positions of the sheath 30 and the catheter 10 thereby exposing a length of the balloon 20.

In FIG. 2 is shown a close-up of the sheath 30 with the inverting sleeve 41 on the interior of the sheath and a balloon 20 on the interior of the inverting sleeve 41. The sheath 30 is slidably disposed around the catheter 10 with the sleeve 41 and balloon attached to the catheter distal end 14. Thus, on the distal end of the device are three layers of materials: the sheath 30, the inverting sleeve 41, and the balloon 20.

FIG. 3. illustrates an exemplary embodiment of the sheath 30 in greater detail. Sheath 30 has a lip 36 at the distal end 34 that defines a sheath distal opening 38. On the interior of the sheath at the distal end is an inner surface 31 and on the exterior is an outer surface 33. Also shown in FIG. 3 is an aperture 35 through which may pass a strand 42 that extends from the sleeve 41 to the proximal end of the catheter (see FIG. 1). In certain embodiments, the sheath has a plurality of apertures. For example, in certain embodiments, the sheath has 2-4 apertures. In still other embodiments, the sheath has 2 apertures.

As shown in FIG. 2, in the inverting tether system of the invention the inverting sleeve 41 generally has a first end 44, a second end 48, and a middle portion 46. The first end 44 is operatively connected to the catheter distal end 14 between the balloon 20 and the sheath 30. The second end 48 is operatively connected to the retraction cuff 60 (e.g., with strands 42). Because the sheath 30 and the middle portion 46 of the inverting sleeve are slidable relative to each other, the middle portion 46 variably and movably extends along the inner and outer surfaces of the sheath distal end 34, through the sheath distal opening 38, inverting over the lip 36 of the sheath distal end 34, and along the outer surface 33 of the sheath distal end. Depending on the state of deployment of the balloon, a greater or lesser amount of the middle portion 46 of the inverting sleeve will extend along the inner surface 31 and outer surface 33 of the sheath distal end 34. When the balloon is in a deployed state, a greater amount of the middle portion 46 will extend along the outer surface 33 of the sheath distal end 34 than when the balloon is not deployed. Conversely, when the balloon is deployed a lesser amount of the middle portion 46 of the inverting sleeve 41 will extend along the inner surface 31 of the sheath distal end 34 than when the balloon is not deployed.

FIG. 4 illustrates the inverting sleeve 41 and catheter 10 in one embodiment of the inverting tether system (the sheath 30 and balloon 20 are omitted for clarity). In the embodiment in FIG. 4, the first end 44 of the sleeve 41 is attached to the catheter distal end 14 to form an operative connection. The configuration in FIG. 4 shows the inverting sleeve 41 with a fold 45, like a rolled-up sleeve. When the sheath 30 surrounds the sleeve 41, the fold 45 is formed over the lip 36 by the middle portion 46 passing through the opening 38 and folding back over in the proximal direction.

Figure 9:
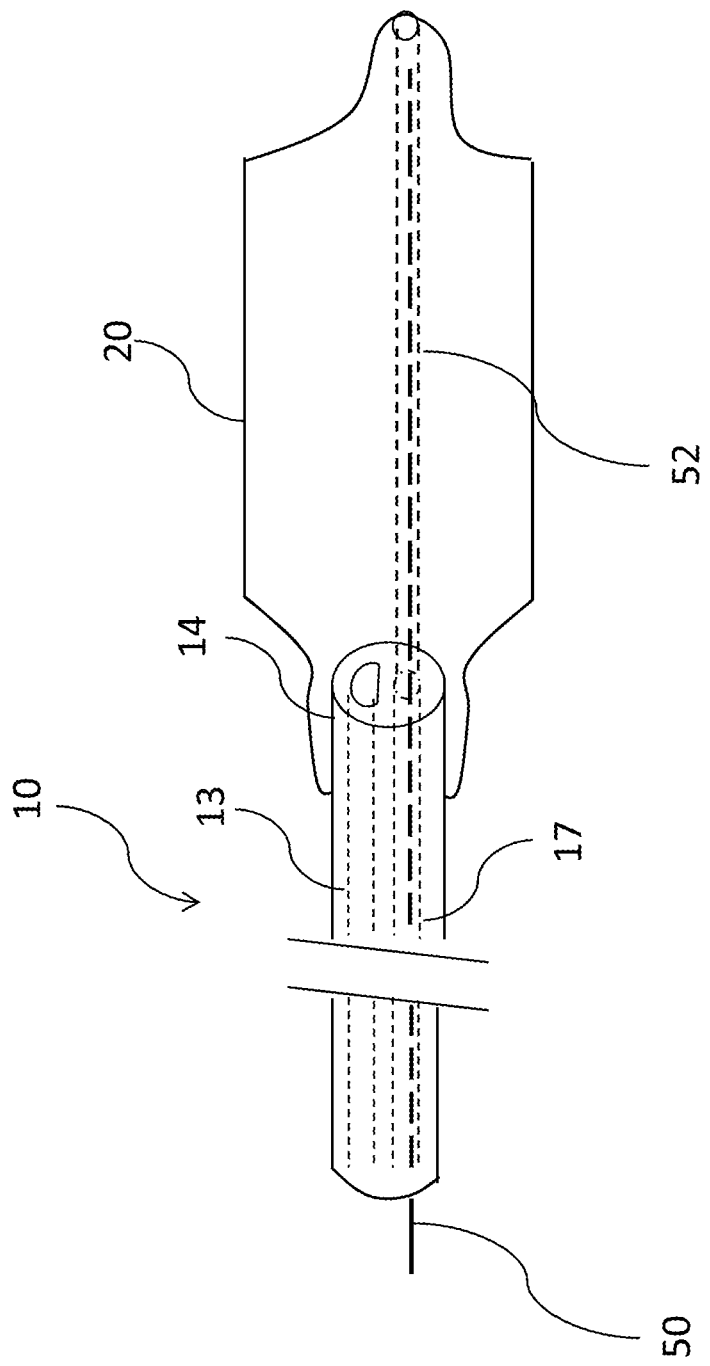
FIG. 9 illustrates a catheter with a wireguide lumen and an inflation lumen with a balloon attached at the distal end of the catheter.

In the embodiment of FIG. 4, the catheter 10 has a distal opening 18 that is in communication with an internal lumen 15 (i.e., a strand lumen) and a proximal opening 16. The openings 16 and 18 and the strand lumen 15 form a channel through which may pass a strand 42 that extends from the sleeve 41 to the retraction cuff 60. The distal opening 18 aligns with (i.e., is in communication with) the aperture 35 such that the strand 42 passes through the aperture 35 and the opening 18 and into the lumen 15. In certain embodiments, the catheter 10 has at least one distal opening 18 and one proximal opening 16. In other embodiments, the catheter 10 has a plurality of distal and proximal openings 18 and 16, respectively. For example, in certain embodiments, the catheter 10 has 2-4 distal openings 18. In still other embodiments, the catheter 10 has 2 distal openings 18. In general, the number of distal openings 18 corresponds with the number of apertures 35, proximal openings 16, lumens 15, and strands 42. In yet other embodiments, multiple strands 42 may join into a single strand that connects to the retraction cuff 60 by passing through a single aperture 35, distal opening 18, internal lumen 15, and proximal opening 16. In preferred embodiments, the distal opening 18 has an elongated shape to accommodate movement of the catheter 10 in the distal direction while avoiding the strand 42 becoming bound in the distal opening 18. Although an internal lumen 15 is shown in FIG. 4, the channel through which the strand passes may be open or partially open on the exterior of the catheter. For example, the channel may have walls and a floor formed in the side of the catheter with intervening bridging elements or a cage-type structure that restrain the strands within the channel. The catheter 10 in FIG. 4 also has an inflation lumen 13. Optionally, the catheter 10 includes a wire guide lumen 17 in addition to an inflation lumen 13, one possible configuration being shown in FIG. 9. Also shown generally in FIG. 9 is a wire guide 50 and a single lumen shaft 52 that allows extension of the wire guide lumen through the balloon 20. The single lumen shaft 52 may be bonded to the distal end 14 of the catheter 10 to maintain the wire guide lumen 17 through to the distal end of the balloon.

In FIG. 5 is shown the catheter 10, the sleeve, and the balloon 20 without the surrounding sheath 30. As can be seen in FIG. 5, the inverting sleeve attaches at the first end 44 to the catheter distal end 14, and the inverting sleeve surrounds the balloon 20. In FIG. 5, the inverting sleeve is shown surrounding substantially all of the balloon 20. As the balloon 20 is deployed by application of a pulling force on the second end 48 of the inverting sleeve, more of the balloon 20 will be exposed outside the sheath 30.

The inverting tether system is not limited to the embodiments explicitly shown and described herein. For example, although the inverting sleeve is shown as a continuous piece of material, the inverting sleeve may use any material that is sufficiently compliant and flexible to fold over the lip of the sheath while having the strength to exert a pulling force on the lip and the catheter distal end. Thus, the middle portion of the inverting sleeve may alternatively be a mesh material or may be an extension of the strands 42 in the distal direction to attach to the catheter distal end 14. In certain embodiments, the first end 44, second end 48, and middle portion 46 of the sleeve together comprise a plurality of strands that extend from the retraction cuff 60 along the outer surface 33 of the sheath distal end 34, over the lip 36, along the inner surface 31 of the sheath distal end 34 and into attachment with the catheter distal end 14. In other embodiments, the inverting sleeve 41, including the first end 44, second end 48, and middle portion 46, comprises a single continuous piece of material, such as a fabric. In certain embodiments, the first end 44 of the inverting sleeve 41 attaches directly to the catheter distal end 14 by, for example, heat bonding, adhesive, or other bonding/fastening technique/mechanism well-known in the arts. In other embodiments, a second plurality of strands 49 (FIG. 6) form an operative connection between first end 44 and the catheter distal end 14. In general, the operative connection between the first end 44 of the inverting sleeve 41 and the catheter distal end 14 may use any type of bridging or connecting material including sutures, threads, strings, wires, mesh, fabric, polymer, etc.

Since the inverting sleeve 41 operatively attaches to the catheter distal end 14 and folds back over the lip 36 of the sheath distal end 34, the application of a pulling force on the sleeve 41 in the proximal direction causes the sleeve 41 to contact the lip 36 of the sheath 30 and to result in pulling forces in opposing directions on the lip 36 of the sheath 30 and the catheter distal end 14. Pulling on the sleeve 41 produces a first pulling force that is applied to the lip 36 of the sheath 30 and a second pulling force that is applied simultaneously to the catheter distal end 14. Holding the sheath 30 in place while pulling on the sleeve 41 produces a forward (i.e., distal) movement of the catheter 10 and balloon 20 by the force of the sleeve 41 pulling the catheter 10 out of the sheath 30. The lip 36 of the sheath 30 acts as a pivot point whereby holding the sheath 30 in place translates the pulling force from the sheath 30 to the catheter 10. The pulling force is maintained until a desired length of balloon 20 has been exposed for a given procedure. In an alternative method of operation, the catheter 10 may be held in place while a pulling force is applied to the sleeve 41, thereby resulting in a proximal displacement of the sheath 30 to expose a length of balloon 20. In either case, the exposed balloon 20 may then be inflated using known techniques to dilate a region of stenosis.

In operation, typically a user will hold the sheath 30 in place while pulling in the proximal direction on the retraction cuff 60. The retraction cuff 60 is operatively connected to the inverting sleeve 41, for example, by a first plurality of strands 42. Thus, pulling on the retraction cuff 60 serves to produce a force that pulls the inverting sleeve 41 in the proximal direction, which in turn pulls the distal end 14 of the catheter 10 and the balloon 20 in the distal direction, thereby exposing a length of balloon 20 through the sheath distal end 34. As explained above, the catheter 10 may alternatively be held in place while the sheath 30 is allowed to slide proximally along the catheter shaft.

Figure 7:
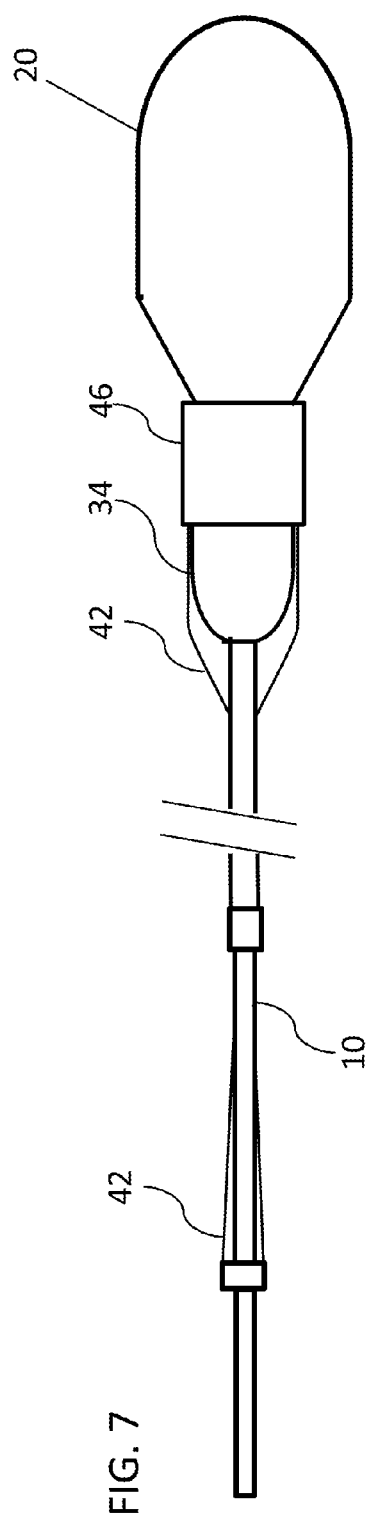
FIG. 7 illustrates an exemplary embodiment of an adjustable length balloon dilatation catheter with the balloon in a deployed state.
Figure 8:
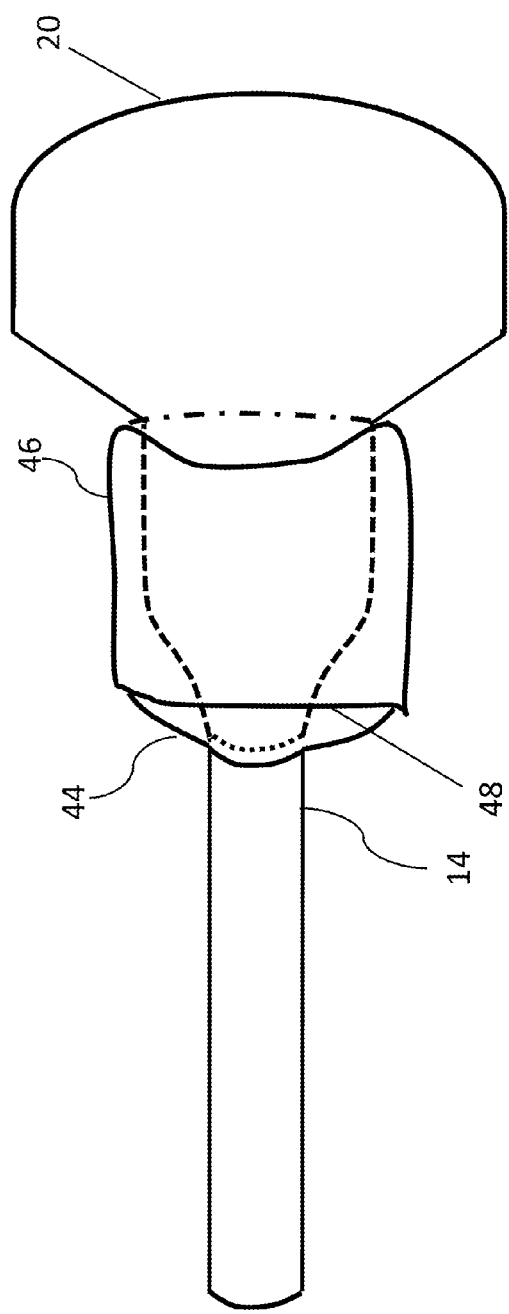
FIG. 8 illustrates the catheter, the balloon, and the inverting sleeve without the sheath where the balloon is in a deployed state.

FIG. 7 illustrates a configuration of the device after the sleeve 41 has been retracted proximally by the strands 42 and retraction cuff 60, thereby pulling distally on the catheter 10 at the point where the first end 44 of the sleeve 41 is attached to the catheter distal end 14. As can be seen, the pulling force on the sleeve 41 acts to expose a length of balloon 20, which can then be inflated as shown. In FIG. 8 is another depiction of a balloon 20 in a deployed and inflated state but where the sheath 30 and strands 42 have been omitted for clarity.

The balloon 20 may be resheathed by deflating the balloon and advancing the sheath 30 through the use of the grip 70 while holding the catheter 10 in place. This process advances the sheath 30 back over the inverting sleeve 41 and the deflated balloon 20. Alternatively, the sheath 30 may be held in place while pulling on the catheter 10 in the proximal direction to pull the inverting sleeve 41 and balloon 20 back into the sheath 30.

The working length of the balloon is generally at least about 2 cm, preferably about 2 cm to 8 cm. The inflated diameter of the balloon may range from about 5 mm to about 15 mm.

The catheter shaft, the balloon and the sheath can be formed from conventional materials such as melt processable thermoplastic polymers, e.g. polyethylene, polyethylene terephthalate, polyester-polyamide such as Hytrel® and an ionomer such as Surlyn®. The sheath can be formed in a laminate construction, e.g. where one layer of the laminate is a relatively high strength to withstand the balloon inflation pressure without significant expanding, e.g. polyethylene terephthalate or a high density polyethylene and another layer is a relatively low strength but more flexible to provide good flexibility for tracking, e.g. a polyester-polyamide such as Hytrel®, a low density polyethylene or a suitable polyurethane. Generally, the more compliant the balloon, the less strength needed in the sheath.

The inverting sleeve can be formed of a medical grade elastic material such as silicone, polyurethane, a copolymer of these, or other elastomeric material commonly used in interventional catheters. The inner surface of the inverting sleeve may have a somewhat tacky surface texture or property.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A medical device comprising:
    a catheter, the catheter comprising a catheter proximal end, a catheter distal end, an inflation lumen, and a catheter external surface;
    a balloon, the balloon being attached to the catheter distal end in fluid communication with the inflation lumen;
    a sheath, the sheath comprising a sheath proximal end and a sheath distal end, the sheath being slidably disposed around the catheter and the balloon, the sheath distal end comprising an inner surface, an outer surface, and a lip that defines a sheath distal opening;
    a retraction cuff, the retraction cuff being slidably disposed on the catheter external surface proximal to the sheath proximal end and capable of being actuated in the proximal direction along a catheter longitudinal axis; and
    an inverting sleeve, the inverting sleeve having a first end, a second end, and a middle portion, the first end being operatively connected to the catheter distal end between the balloon and the sheath, the second end being operatively connected to the retraction cuff, and the middle portion variably extending along the inner surface of the sheath distal end, through the sheath distal opening, inverting over the lip of the sheath distal end, and along the outer surface of the sheath distal end.

2. The device of claim 1, wherein the retraction cuff is operably connected to the second end of the inverting sleeve by a first plurality of strands.

3. The device of claim 2, wherein:
    the sheath further comprises a plurality of apertures, the first plurality of strands extending from the second end of the inverting sleeve along an exterior of the sheath through the plurality of apertures, along an interior of the sheath, and connecting to the retraction cuff.

4. The device of claim 3, wherein:
the catheter further comprises a plurality of channels wherein the first plurality of strands extend along the interior of the sheath through the plurality of channels.

5. The device of claim 4, wherein each channel of the plurality of channels comprises a strand lumen, a proximal opening, and a distal opening, the distal opening being in communication with the strand lumen and an aperture of the plurality of apertures of the sheath.

6. The device of claim 2 wherein the first plurality of strands comprises 2-4 strands.

7. The device of claim 1, wherein the operative connection between the catheter distal end and the first end of the inverting sleeve comprises a second plurality of strands.

8. The device of claim 1, wherein the first end of the inverting sleeve is connected to the catheter distal end.

9. The device of claim 1, wherein the sheath further comprises a grip, the grip being located on the sheath proximal end.

10. The device of claim 1 comprising a first configuration wherein substantially all of the balloon is surrounded by the sheath.

11. The device of claim 1 comprising a second configuration wherein a portion of the balloon extends through the sheath distal opening.

12. The device of claim 1, wherein the catheter further comprises a wire guide lumen.

* * * * *

UNITED STATES PATENT AND TRADEMARK OFFICE
CERTIFICATE OF CORRECTION

PATENT NO. : 9,526,875 B2
APPLICATION NO. : 14/528793
DATED : December 27, 2016
INVENTOR(S) : Kamel et al.

Page 1 of 1

It is certified that error appears in the above-identified patent and that said Letters Patent is hereby corrected as shown below:

On the Title Page

Item (54) and in the Specification, Column 1, Line 2, in the Title, please delete "DILATION" and replace with -- DILATATION --.

Signed and Sealed this
Third Day of April, 2018

Andrei Iancu
*Director of the United States Patent and Trademark Office*